US010401456B2

(12) United States Patent
De Weerdt et al.

(10) Patent No.: US 10,401,456 B2
(45) Date of Patent: Sep. 3, 2019

(54) PARALLEL MR IMAGING WITH NYQUIST GHOST CORRECTION FOR EPI (71) Applicant: KONINKLIJKE PHILIPS N.V., Eindhoven (NL)

(72) Inventors: Elwin De Weerdt, Eindhoven (NL); Zhaolin Chen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 111 days.

(21) Appl. No.: 15/505,256

(22) PCT Filed: Aug. 18, 2015

(86) PCT No.: PCT/EP2015/068973
§ 371 (c)(1),
(2) Date: Feb. 21, 2017

(87) PCT Pub. No.: WO2016/026872
PCT Pub. Date: Feb. 25, 2016

(65) Prior Publication Data
US 2018/0238986 A1    Aug. 23, 2018

(30) Foreign Application Priority Data
Aug. 22, 2014  (EP) .................................. 14181994

(51) Int. Cl.
G01R 33/561    (2006.01)
G01R 33/565    (2006.01)
G01R 33/48     (2006.01)
G01R 33/341    (2006.01)
A61B 5/055     (2006.01)

(52) U.S. Cl.
CPC .......... G01R 33/5611 (2013.01); A61B 5/055 (2013.01); G01R 33/341 (2013.01); G01R 33/4818 (2013.01); G01R 33/56545 (2013.01); G01R 33/56554 (2013.01)

(58) Field of Classification Search
USPC .......................... 324/300–322; 600/407–435
See application file for complete search history.

(56) References Cited

U.S. PATENT DOCUMENTS 6,326,786 B1   12/2001 Pruesssmann et al.
6,700,374 B1    3/2004 Wu et al.
(Continued)

OTHER PUBLICATIONS

Clare, "Interative Nyquist Ghost Correction for Single and Multishot EPI Using an Entropy Measure" Proc. Intl. Soc. Mag. Reson, Med. 2003.
(Continued)

Primary Examiner — Melissa J Koval
Assistant Examiner — Tiffany A Fetzner

(57) ABSTRACT

A method of parallel MR imaging includes subjecting the portion of the body (10) to an imaging sequence of at least one RF pulse and a plurality of switched magnetic field gradients. The MR signals are acquired in parallel via a plurality of RF coils (11, 12, 13) having different spatial sensitivity profiles within the examination volume. The method further includes deriving an estimated ghost level map from the acquired MR signals and from spatial sensitivity maps of the RF coils (11, 12, 13), and reconstructing a MR image from the acquired MR signals, the spatial sensitivity maps, and the estimated ghost level map.

9 Claims, 3 Drawing Sheets

EPI PHANTOM IMAGES

NOISE AMPLIFICATION MAPS

(56) References Cited

U.S. PATENT DOCUMENTS

| | | | |
|---|---|---|---|
| 7,535,222 B2 | 5/2009 | Bammer et al. | |
| 8,354,844 B2* | 1/2013 | Zaitsev | G01R 33/5611 324/307 |
| 9,581,671 B2* | 2/2017 | Dannels | G01R 33/56554 |
| 9,664,760 B2* | 5/2017 | James | A61B 5/055 |
| 9,760,979 B2* | 9/2017 | Chen | G01R 33/543 |
| 9,886,745 B2* | 2/2018 | Chen | G01R 33/543 |
| 10,061,003 B2* | 8/2018 | James | A61B 5/055 |
| 2009/0285463 A1* | 11/2009 | Otazo | G06T 3/4053 382/131 |
| 2011/0148410 A1* | 6/2011 | Zaitsev | G01R 33/5611 324/309 |
| 2014/0002078 A1* | 1/2014 | Chen | G01R 33/543 324/309 |
| 2015/0154741 A1* | 6/2015 | Chen | G01R 33/543 348/77 |
| 2015/0241537 A1* | 8/2015 | Dannels | G01R 33/56554 324/309 |
| 2016/0231409 A1* | 8/2016 | Taviani | G01R 33/5611 |
| 2017/0030986 A1* | 2/2017 | James | G01R 33/4818 |
| 2017/0261584 A1* | 9/2017 | James | A61B 5/055 |
| 2017/0307716 A1* | 10/2017 | De Weerdt | G01R 33/4824 |
| 2018/0238986 A1* | 8/2018 | De Weerdt | G01R 33/5611 |

OTHER PUBLICATIONS

Kim et al Automatic Correction of Echo-Planar Imaging (EPI) Ghosting Artifacts in Real Time Interactive Cardiac MRI Using Sensitivity Encoding., Journal of Magnetic Resonance Imaging, vol. 27 p. 239-245 (2008).

Lustig et al Sparse MRI: The Application of Compressed Sensng for Rapid MR Imaging: Magnetic Resonance in Med. vol. 58, p. 1182-1195 (2007).

Winkelmann et al "Ghost Artifact Removal Using a Parallel Imaging Approach" Magnetic Resonance in Med. vol. 54, No. 4 Jan. 1, 2005 p. 1002-1009.

Peter Kellman et al: "Phased array ghost elimination",NMR in Biomedicine, vol. 19, No. 3,Jan. 1, 2006 (Jan. 1, 2006), pp. 352-361.

Larkman DJ et al: "Consistency based ghost busting (CBGB)",Proceedings of the International Society for Magnetic Resonance in Medicine, ISMRM,Joint Annual Meeting ISMRM-ESMRMB, Berlin,Germany, May 19-25, 2007,May 5, 2007 (May 5, 2007), p. 987.

Chang Z, Xiang Q-S: "Highly accelerated MRI by sensitivity encoding with skipped phase encoding and edge deghosting (SEN-SPEED)",Proceedings of the International Society for Magnetic Resonance in Medicine, ISMRM, 13th Scientific Meeting and Exhibition, Miami Beach, Florida, USA, May 7-13, 2005, Apr. 23, 2005 (Apr. 23, 2005), p. 2448.

Kellman et al "Ghost Artifact Cancellation Using Phased Array Processing" Magnetic Resonance in Med. 46, p. 335-343 (2001).

Yun et al "Ghost Artifact Reduction in EPI (Echo Planar Imaging) With Sensitivity Encodign (Sense) Proc. Intl. Soc. Mag Reson Med. 13 (2005) p. 2179.

Schmithorst et al "Simultaneous Correction of Ghost and Geometric Distortion Artifact in EPI Using a Multi-Echo Reference Scan" NIH Author Manuscript Jan. 31, 2006.

\* cited by examiner

Fig. 1

EPI PHANTOM IMAGES  Fig. 2

NOISE AMPLIFICATION MAPS  Fig. 3

Fig. 4

PARALLEL MR IMAGING WITH NYQUIST GHOST CORRECTION FOR EPI

CROSS REFERENCE TO TELATED APPLICATIONS

This application is a U.S. national phase application of International Application No. PCT/EP2015/068973, filed on Aug. 18, 2015, which claims the benefit of EP Application Serial No. 14181994.6 filed on Aug. 22, 2014 and is incorporated herein by reference.

FIELD OF THE INVENTION

The invention relates to the field of magnetic resonance (MR) imaging. It concerns a method of MR imaging of at least a portion of a body. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system on which the measurement is based. The magnetic field splits different energy levels for the individual nuclear spins in dependence on the magnetic field strength and the specific spin properties. The spin system can be excited (spin resonance) by application of an electromagnetic alternating field (RF field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate radio frequency (RF pulse) while the corresponding $B_1$ magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic RF pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° RF pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data are usually acquired along multiple lines with different phase encoding values to achieve sufficient coverage. Each line is digitized during read-out by collecting a number of samples. A set of k-space data is converted to a MR image by means of Fourier transformation.

Echo planar imaging (EPI) is a known rapid MR imaging technique which is used to produce MR images at high acquisition rates, typically several images per second. It has been found particularly useful in diffusion imaging, for functional magnetic resonance imaging (fMRI), in dynamic imaging etc. The basic idea of EPI is to completely sample k-space in a single repetition (single-shot EPI) during one $T_2$ decay, or in multiple shots (multi-shot EPI). In single-shot EPI, all k-space lines are acquired during multiple magnetic field gradient reversals, producing multiple gradient echo signals in a single acquisition after a single RF excitation pulse, i.e., in a single measurement or "shot". In multi-shot EPI, the acquisition of MR signals is divided into multiple shots. In this case, k-space is segmented by multiple acquisitions. Multi-shot EPI is also referred to as segmental EPI.

MR images reconstructed from EPI acquisitions tend to suffer from so-called "Nyquist ghosting". In the case of single-shot EPI, the ghost image is shifted by half a field of view in the phase encoding direction. In multi-shot EPI, the ghosting pattern can be more complex. The Nyquist ghost artifacts are caused mainly by induced eddy currents and system timing errors with respect to the positive and negative magnetic field gradient lobes. These errors are associated with the MR scanner hardware.

Several methods are known in the art for correcting the Nyquist ghost artifacts, for example based on information gained from reference scans or navigator echoes acquired together with image data. Reference scans may be employed to determine systematic phase errors of the MR signals induced by the imperfections of magnetic field gradient switching. The imaging data can then be corrected accordingly. Navigator echoes can be used, preferably in dynamic EPI scans, to track the varying delays of magnetic field gradient switching.

A drawback of these known techniques is that the applied corrections are generally not able to completely remove the Nyquist ghosts. This is caused by the magnetic field gradient switching delays changing over time (without being re-estimated correctly), application of only a one-dimensional phase correction (in the phase encoding direction), missing compensation of higher order terms etc.

Other purely "data driven" approaches exist that do not require either a reference scan or navigators (see e.g. Clare, "Iterative Nyquist Ghost Correction for Single and Multi-shot EPI using an Entropy Measure", Proc. Intl. Soc. Mag. Reson. Med. 11, 2003). A drawback of such techniques is that they tend to require a prohibitively long reconstruction time. The ISMRM abstract ISMRM2007-987(D3) concerns the problem of Nyquist ghosting in single-shot EPI and provides a de-ghosting in the image domain driven by a metric based on coil consistency.

SUMMARY OF THE INVENTION

From the foregoing it is readily appreciated that there is a need for an efficient MR imaging technique that provides an improved correction of Nyquist ghost artifacts.

In accordance with the invention, a method of parallel MR imaging of at least a portion of a body placed in the examination volume of a MR device is disclosed. The method comprises the steps of:
a) subjecting the portion of the body to an imaging sequence of at least one RF pulse and a plurality of switched magnetic field gradients (preferably single-shot or multi-shot EPI), wherein MR signals are acquired in parallel via a plurality of RF coils having different spatial sensitivity profiles within the examination volume,
b) deriving an estimated ghost level map from the acquired MR signals and from spatial sensitivity maps of the RF coils,
c) reconstructing a MR image from the acquired MR signals, the spatial sensitivity maps, and the estimated ghost level map.

Parallel imaging techniques are known in the art for accelerating MR signal acquisition. A method in this category is SENSE (Sensitivity Encoding). SENSE and other parallel imaging techniques use undersampled k-space data acquisition obtained from multiple RF receiving coils in parallel. In these methods, the (complex) signal data from the multiple RF receive coils are combined with complex weightings in such a way as to suppress undersampling artifacts (aliasing) in the finally reconstructed MR images. This type of complex RF coil array signal combination is sometimes referred to as spatial filtering and includes combining in the k-space domain or in the image domain (in SENSE), as well as methods which are hybrids. In SENSE imaging, spatial sensitivity maps of the RF coils are typically estimated from low-resolution reference data obtained by a SENSE reference scan. This coil sensitivity information is then used to "unwrap" aliased pixels in image space using a direct inversion algorithm.

According to the invention, a parallel acquisition and reconstruction technique (like SENSE, for example), which employs spatial sensitivity maps of the RF coils maps for combining the MR signals received via the array of RF coils, is used for suppression of Nyquist ghosts.

The gist of the invention is the application of two or more iterations of the parallel reconstruction algorithm, wherein a ghost level map indicating the level of ghosting for each image position is derived from the acquired MR signal data and the spatial sensitivity maps of the RF coils in a first iteration (step b). The estimated ghost level map is then applied in a subsequent iteration of the parallel reconstruction algorithm to reconstruct the MR image, wherein the estimated ghost level map is used in step c) to eliminate the ghost artifacts in the reconstructed MR image.

Preferably, the method of the invention further comprises the step of spatially smoothing the estimated ghost level map prior to reconstructing the MR image in step c). In this embodiment, the invention is based on the assumption of a spatially smoothly varying ghost level and hence can handle all system imperfections that lead to such a smoothly varying ghost level. The assumption of a constant ghost level in the phase encoding direction is not made according to the invention. The technique is fully n-dimensional, with n being the number of dimensions of the MR signal data. Hence, the technique is superior to conventional one-dimensional phase correction methods. This also means that the technique of the invention is able to remove Nyquist ghost artifacts in multi-shot EPI, where the standard EPI ghost correction methods typically fail.

A further advantage is that the method of the invention does not require the acquisition of reference data for the removal of the Nyquist ghost artifacts. Consequently, the method of the invention provides full Nyquist artefact removal by pure post-processing of the acquired MR signal data, this is, without extending the scan time. Moreover, because no reference data is required, the technique of the invention can be advantageously used in combination with rapid dynamic imaging techniques, such as PROPELLER-DWI etc. It has to be noted, however, that, for example, in cases in which a shortest possible scan time is not essential, the method of the invention may be combined with conventional phase-correction techniques using reference data in order to further improve the level of ghost artefact removal.

In a preferred embodiment of the invention, each of steps b) and c) comprises the simultaneous computation of a MR image and a MR ghost image using a linear inversion method. Linear inversion methods are conventionally applied in known parallel image reconstruction techniques (such as SENSE), for example employing least squares optimisation schemes (like the common Tikhonov regularisation technique). According to the invention, the number of unknowns of the inversion is increased by computing not only the MR image but also the MR ghost image. The ghost level map can then be estimated by computing the ratio of the reconstructed MR ghost image and the reconstructed "true" MR image in step b).

Preferably, the MR image reconstruction in step c) involves regularisation (like in common parallel reconstruction techniques) using an (additional) regularisation constraint that is derived from the smoothed estimated ghost level map. A regularisation parameter (Lagrange factor) determining the weighting of the regularisation constraint in the linear inversion can then be tuned depending on the signal-to-noise ratio (SNR) of the MR image reconstructed in step c). In other words, the reconstruction method is based in this embodiment on a constrained optimization, which optimizes SNR subject to the constraint of removing the Nyquist ghost artifacts, wherein the level of ghost artefact removal may be defined interactively by a user.

Steps b) and c) of the method of the invention may be iteratively repeated in order to successively increase the accuracy of the ghost level map. The regularisation parameter may be varied for increasing the weighting of the regularisation constraint from iteration to iteration. If the inversion problem is to ill-conditioned initially, a preliminary estimate of the ghost level map (for example obtained from a reference measurement) may be used in a first iteration, wherein the iterative scheme then converges to the true ghost level map after one or more further iterations.

As in conventional parallel imaging (such as SENSE), the method of the invention may be combined with undersampling of k-space in order to increase acquisition speed. The method of the invention is able to simultaneously unfold both the undersampling (aliasing) artifacts and the Nyquist ghost artifacts.

The method of the invention is compatible with the known compressed sensing (CS) technique, which may be applied advantageously in steps b) and/or c). In CS theory, a signal data set which has a sparse representation in a transform domain can be recovered from undersampled measurements by application of a suitable regularisation algorithm. The possibility of undersampling leads to a significantly reduced acquisition time. As a mathematical framework for signal sampling and reconstruction, CS prescribes the conditions under which a signal data set can be reconstructed exactly or at least with high image quality even in cases in which the k-space sampling density is far below the Nyquist criterion, and it also provides the methods for such reconstruction. For example, M. Lustig et al. have proposed the application of CS for rapid MR imaging (M. Lustig et al.: "Sparse MRI: The Application of Compressed Sensing for Rapid MR Imaging", Magnetic Resonance in Medicine, 58, 1182-1195, 2007). The estimated ghost level map computed according to the invention can be incorporated as prior information into the CS reconstruction.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, a number of RF coils for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention is preferably implemented by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
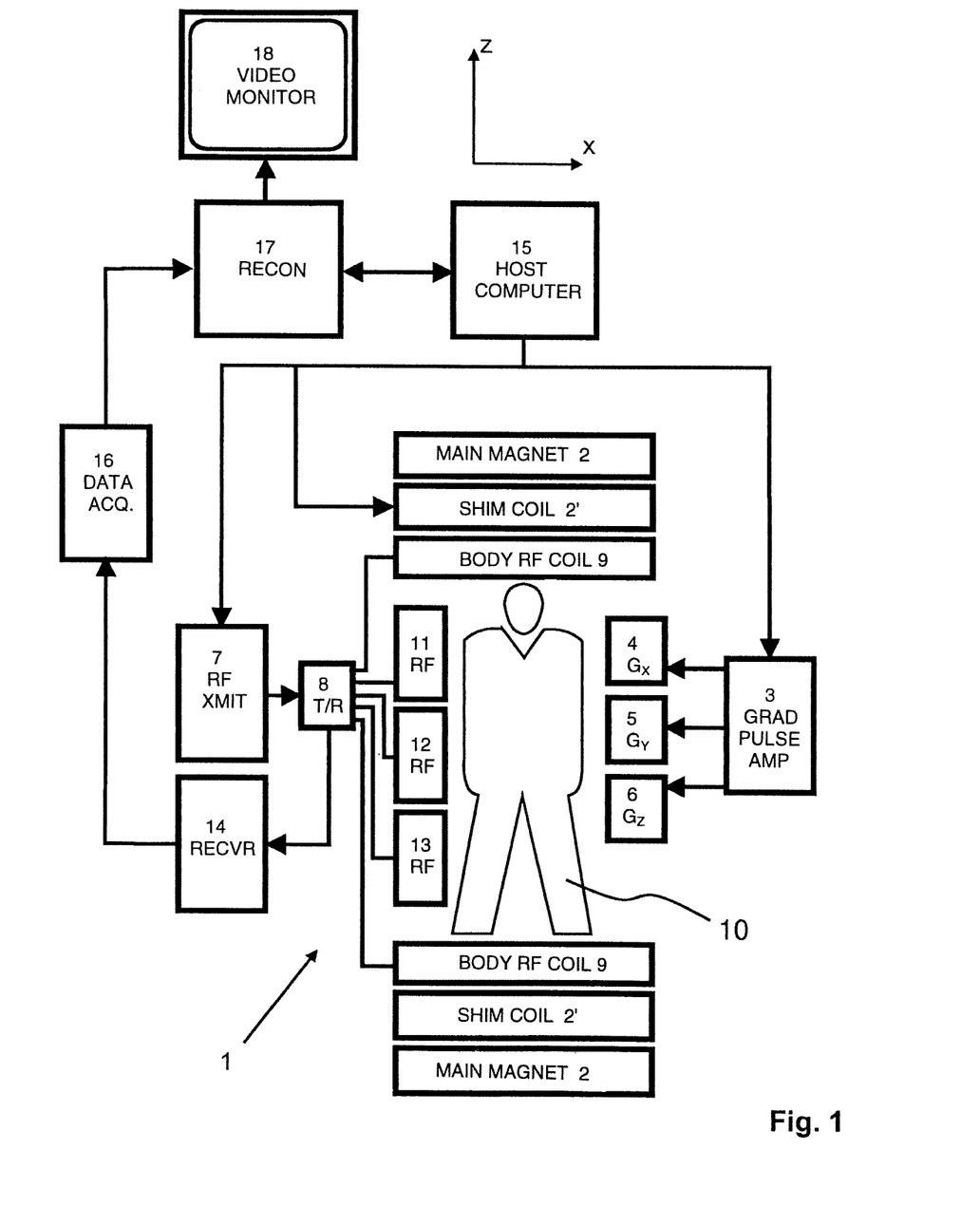
FIG. 1 schematically shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients (also referred to as 'gradient pulses') to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a—body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite magnetic resonance, invert magnetization, refocus resonance, or manipulate resonance and select a portion of a body 10 positioned in the examination volume.

For generation of MR images of regions of the body 10 by means of parallel imaging, a set of local array RF coils 11, 12, 13 having different spatial sensitivity profiles are placed contiguous to the region selected for imaging. The array RF coils 11, 12, 13 are used to receive MR signals induced by body-coil RF transmissions.

The resultant MR signals are picked up by the body RF coil 9 and by the array RF coils 11, 12, 13 and demodulated by a receiver 14 preferably including a pre-amplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies appropriate reconstruction algorithms, such like SENSE. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

According to the invention, the body 10 is subjected to a single-shot or multi-shot EPI sequence, wherein MR signals are acquired in parallel via the array of RF coils 11, 12, 13 having different spatial sensitivity profiles within the examination volume. As in conventional SENSE imaging, spatial sensitivity maps of the RF coils are determined from low-resolution reference data obtained by a SENSE reference scan. An estimated ghost level map indicating the level of ghosting for each image position is derived from the acquired MR signals and from the spatial sensitivity maps of the RF coils 11, 12, 13 by a first SENSE unfolding step based on the following system of equations:

$$m_j(x) = \Sigma_i S_j(x_i) p_{obj}(x_i) + S_j(x_i + FOV/2) p_{ghost}(x_i),$$

wherein $m_j(x)$ is the MR image (prior to unfolding) reconstructed from MR signals acquired via one of the RF coils 11, 12, 13, with j indicating the respective RF coil. $S_j(x)$ is the spatial sensitivity map of RF coil j, $p_{obj}(x)$ is the signal contribution from the object (the body 10), and $p_{ghost}(x)$ is the signal contribution from the ghost image. FOV is the size of the field of view (i.e. the "folded" field of view equal to the planned FOV divided by the acceleration factor of the parallel imaging technique). The formula takes into account that the signal contribution from the Nyquist ghost is weighted by the spatial sensitivity map shifted by one-half field of view. Tikhonov regularisation may be used in this unfolding step as in common SENSE reconstruction. This kind of regularisation provides information about the expected level of output signal per image position. This includes information as to the image area in which the object is positioned and the background. Using this information improves the SNR. The standard Tikhonov regularisation is also applied for the ghost image $p_{ghost}(x_i)$. It is based on the same data, with the only difference that the ghost image is shifted by one-half FOV to account for the different spatial location of the ghost image. The estimated ghost level map g(x) is then calculated as:

$$g(x) = p_{ghost}(x)/p_{obj}(x)$$

As a next step, spatial smoothing is applied to g(x) in order to obtain the low frequency information about the ghost level. In this way, the assumption that the ghost level is spatially smoothly varying is introduced into the reconstruction method. A further SENSE unfolding step is then performed based on the above system of equations and using the following regularisation constraint:

$$g(x) p_{obj}(x) - p_{ghost}(x) = 0,$$

wherein g(x) is the smoothed estimated ghost level map. The finally reconstructed MR image (without Nyquist ghost artifacts) then corresponds to $p_{obj}(x)$. A regularisation parameter (Lagrange factor) determining the weighting of the regularisation constraint in the second unfolding step is tuned depending on the signal-to-noise ratio of the MR image. If the constraint is strongly weighted this results in $p_{ghost}(x) = g(x) p_{obj}(x)$ and the increase of the noise level of the reconstructed MR image is minimal. If the weighting is low, in contrast, the level of Nyquist ghosting is minimized (since any errors in the computation of g(x) are shifted into $p_{ghost}(x)$). However, SNR is decreased in the final image.

Optionally, further iterations over the above two SENSE unfolding steps can be performed, wherein the weighting of the regularisation constraint may be increased from iteration to iteration. In this way, the estimated ghost level map can be determined more and more accurately. If the inversion problem is too ill-conditioned in the first step, which may be the case if the SENSE acceleration factor is large, the iteration may start with a pre-set ghost level map, for example assuming a fixed ghost level or a ghost level map obtained from an initial reference measurement.

The total reconstruction time required by the method of the invention is only marginally increased vis-a-vis conventional SENSE, since the unfolding procedure constitutes only a small part of the total reconstruction. Moreover, the modified unfolding of the invention typically requires only a limited number of iterations.

Figure 2:
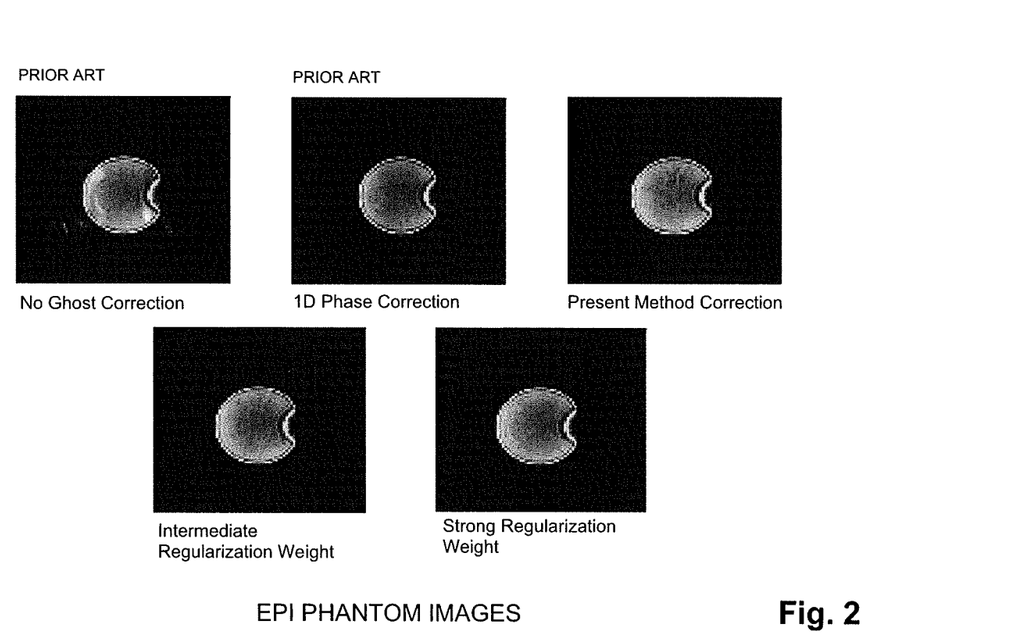
FIG. 2 shows EPI images of a phantom reconstructed conventionally and according to the method of the invention.

FIG. 2 shows EPI images of a phantom acquired with SENSE factor 2. The upper left image is reconstructed without Nyquist ghost correction. The image shows strong ghost artifacts. Conventional one-dimensional phase correction based on a reference measurement is applied in the upper middle image. The level of Nyquist ghosting is substantially reduced. The upper right image is reconstructed according to the method of the invention with a low weighting of the regularisation constraint. An intermediate regularisation weight is applied in the bottom left image, the bottom right image shows the reconstructed MR image using a strong regularisation weight. The images reconstructed according to the invention show different levels of Nyquist ghost suppression.

Figure 3:
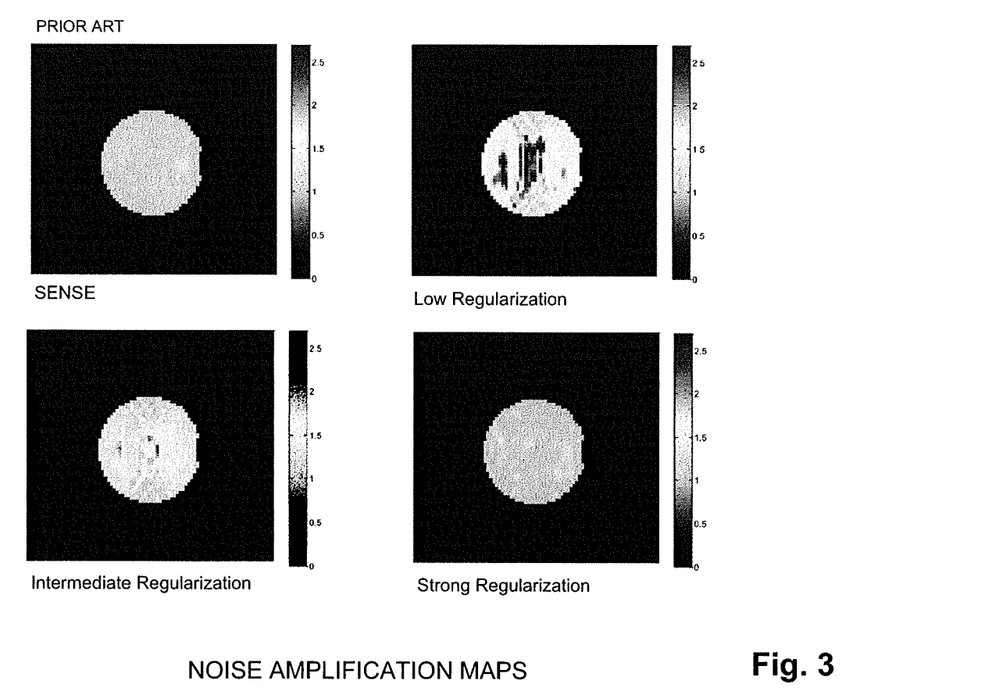
FIG. 3 shows noise amplification maps for different weightings of the regularisation constraint applied according to the method of the invention.

FIG. 3 shows corresponding noise amplification maps. The noise amplification maps are computed according to:

$$NAM(x, y) = \sqrt{\frac{H_{SENSE}(x, y) H_{SENSE}^h(x, y)}{H_{CLEAR}(x, y) H_{CLEAR}^h(x, y)}},$$

wherein $H_{SENSE}(x,y)$ is the combination factor matrix obtained during the SENSE unfolding for image location x, y (size 1×number of RF coils) and $H_{clear}(x,y)$ is the combination factor matrix obtained during standard SENSE unfolding with SENSE factor 1 (CLEAR operation). NAM (x,y) can never be less than 1 and only provides valid information inside the imaged anatomy. The upper left image in FIG. 3 shows NAM(x,y) for conventional SENSE reconstruction. The upper right image corresponds to the modified SENSE unfolding with a low weighting of the regularisation constraint. An intermediate regularisation weight is applied in the bottom left image, the bottom right image shows NAM(x,y) using a strong regularisation weight.

As becomes evident from FIGS. 2 and 3, Nyquist ghosting can be successfully removed by the method of the invention with a minimal/negligible increase of the noise level. The SNR only drops very slightly as compared to standard SENSE reconstruction.

Figure 4:
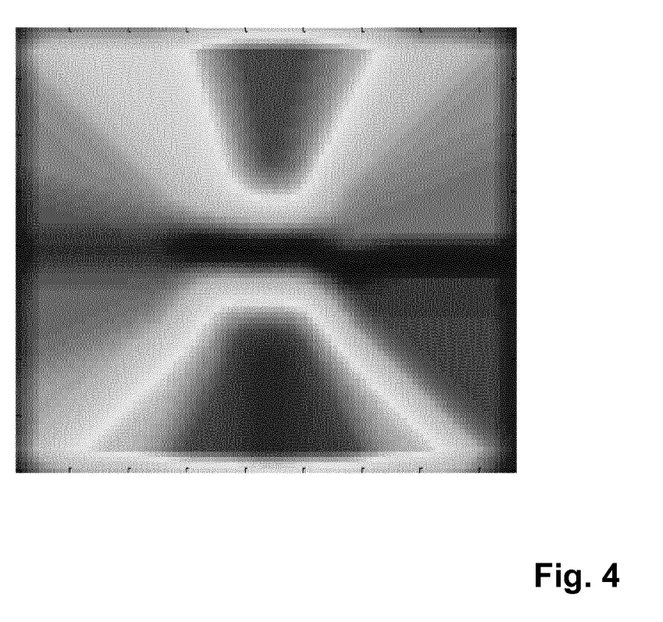
FIG. 4 shows a ghost level map computed according to the invention.

FIG. 4 shows the ghost level map g(x,y) estimated according to the method of the invention. FIG. 4 illustrates that the assumption of a constant ghost level in the phase encoding direction is not made according to the invention. Hence, the technique is superior to one-dimensional phase correction approaches used conventionally for Nyquist ghost removal and thus generally provides an improved image quality.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of parallel MR imaging of at least a portion of a body placed within the examination volume of a MR device, the method comprising the steps of:
   a) subjecting the portion of the body to a single-shot or a multi-shot EPI imaging sequence of at least one RF pulse and a plurality of switched magnetic field gradients, wherein MR signals are acquired in parallel via a plurality of RF coils having different spatial sensitivity profiles with a FOV matrix size doubled to separate Nyquist-ghosts from image information within the examination volume, b) deriving an estimated Nyquist-ghost level map from the acquired MR signals and from spatial sensitivity maps of the RF coils based on solving the following system of equations:

$$m_j(x)=\Sigma_j S_j(x_i)p_{obj}(x_i)+S_j(x_i+FOV/2)p_{ghost}(x_i),$$

wherein $m_j(x)$ is the MR image (prior to unfolding) reconstructed from MR signals acquired via one of the RF coils 11, 12, 13, with j indicating the respective RF coil, $S_j(x)$ is the spatial sensitivity map of RF coil j, $p_{obj}(x)$ is the signal contribution from the object (the body 10), and $p_{ghost}(x)$ is the signal contribution from the ghost image, FOV is the size of the field of view, and the estimated ghost level map g(x) is then calculated as:

$$g(x)=p_{ghost}(x)/p_{obj}(x)$$

and spatially smoothing the estimated Nyquist-ghost level map c) reconstructing a MR image from the same acquired MR signals from which the Nyquist-ghost level map is derived, the spatial sensitivity maps, and the estimated Nyquist-ghost level map and the reconstruction involving regularisation using the regularisation constraint $g(x)p_{obj}(x)-p_{ghost}(x)=0$, that is derived from the smoothed estimated Nyqiust-ghost level map; and iteratively repeating steps b) and c) with the same MR signals to successively increase the accuracy of the ghost level map.

2. The method of claim 1, wherein the estimated ghost level map and/or the MR image is reconstructed in steps b) and/or c) using compressed sensing.

3. The method of claim 1, wherein each of steps b) and c) comprises the computation of a MR image and a MR ghost image using a linear inversion method.

4. The method of claim 3, wherein a regularisation parameter determining the weighting of the regularisation constraint in the linear inversion is tuned depending on a signal-to-noise ratio of the MR image reconstructed in step c).

5. The method of claim 1, wherein the MR signals are acquired in step a) with undersampling of k-space.

6. A magnetic resonance (MR) device comprising at least one main magnet coil configured for generating a uniform, study magnetic field within an examination volume, a number of gradient coils configured for generating switched magnetic field gradients in different spatial directions within the examination volume, at least one RF coil configured for generating RF pulses in the examination volume, a plurality of RF coils having different spatial sensitivity profiles within the examination volume configured for receiving MR coils from at least a portion of a body of a patient positioned in the examination volume, a control unit configured for controlling the temporal succession of RF pulses and switched magnetic field gradients, and a reconstruction unit configured for reconstructing MR images from the received MR signals, wherein the MR device is arranged to perform the following steps:

a) subjecting the portion of the body to a single-shot or multi-shot EPI imaging sequence of at least one RF pulse and a plurality of switched magnetic field gradients, wherein MR signals are acquired in parallel via the RF coils, b) deriving an estimated Nyquist-ghost level map from the acquired MR signals and from spatial sensitivity maps of the RF coils and spatially smoothing the estimated ghost level map, wherein the Nyquist-ghose level map is derived from the following system of equations:

$$m_j(x)=\Sigma_j S_j(x_i)p_{obj}(x_i)+S_j(x_i+FOV/2)p_{ghost}(x_i),$$

wherein $m_j(x)$ is the MR image (prior to unfolding) reconstructed from MR signals acquired via one of the RF coils 11, 12, 13, with j indicating the respective RF coil, $S_j(x)$ is the spatial sensitivity map of RF coil j, $p_{obj}(x)$ is the signal contribution from the object (the body 10), and $p_{ghost}(x)$ is the signal contribution from the ghost image, FOV is the size of the field of view, and the estimated ghost level map g(x) is then calculated as:

$$g(x)=p_{ghost}(x)/p_{obj}(x)$$

and spatially smoothing the estimated Nyquist-ghost level map, c) reconstructing a MR image from the acquired MR signals, the spatial sensitivity maps, and the smoothed estimated Nyquist-ghost level map from step b), and the reconstruction involving regularisation using a regularisation constraint $g(x)p_{obj}(x)-p_{ghost}(x)=0$, that is derived from the smoothed estimated Nyquist-ghost level map.

7. The magnetic resonance device of claim 6 wherein the MR device is further arranged to:

iteratively repeat steps b) and c) with the same MR signals to successively increase the accuracy of the Nyquist-ghost level map in the reconstructed MR image.

8. A non-transitory computer-readable medium carrying a computer program which when executed on a computer controls an MR device to:

a) generate a single or a multi-shot EPI imaging sequence of at least one RF pulse and a plurality of switched magnetic field gradients, and acquiring MR signals in parallel via a plurality of RF coils having different spatial sensitivity profiles, b) derive an estimated Nyquist-ghost level map from the MR signals acquired in step a) and from spatial sensitivity maps of the RF coils, and spatially smoothing the estimated ghost level map, wherein the Nyquist-ghose level map is derived from the following system of equations:

$$m_j(x)=\Sigma_j S_j(x_i)p_{obj}(x_i)+S_j(x_i+FOV/2)p_{ghost}(x_i),$$

wherein $m_j(x)$ is the MR image (prior to unfolding) reconstructed from MR signals acquired via one of the RF coils 11, 12, 13, with j indicating the respective RF coil, $S_j(x)$ is the spatial sensitivity map of RF coil j, $p_{obj}(x)$ is the signal contribution from the object (the body 10), and $p_{ghost}(x)$ is the signal contribution from the ghost image, FOV is the size of the field of view, and the estimated ghost level map g(x) is then calculated as:

$$g(x)=p_{ghost}(x)/p_{obj}(x)$$

and spatially smoothing the estimated Nyquist-ghost level map, and c) reconstruct a MR image from the acquired MR signals, the spatial sensitivity maps, and the smoothed estimated Nyquist-ghost level map and the reconstruction involving regularisation using a regularisation constraint $g(x)p_{obj}(x)-p_{ghost}(x)=0$, that is derived from the smoothed estimated Nyquist-ghost level map.

9. The non-transitory computer-readable medium of claim 8, wherein which, when the computer program is executed on the computer, further controls the MR device to:
   iteratively repeat steps b) and c) with the same MR signals to successively increase the accuracy of the Nyquist-ghost level map in the reconstructed MR image.

* * * * *